US010655165B2

(12) United States Patent
Carlson et al.

(10) Patent No.: US 10,655,165 B2
(45) Date of Patent: May 19, 2020

(54) ASYMMETRIC HAIRPIN TARGET CAPTURE OLIGOMERS

(71) Applicant: GEN-PROBE INCORPORATED, San Diego, CA (US)

(72) Inventors: James Carlson, San Diego, CA (US); Reinhold Pollner, San Diego, CA (US); Steven T. Brentano, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 509 days.

(21) Appl. No.: 14/376,128

(22) PCT Filed: Feb. 1, 2013

(86) PCT No.: PCT/US2013/024499
§ 371 (c)(1),
(2) Date: Nov. 11, 2014

(87) PCT Pub. No.: WO2013/116774
PCT Pub. Date: Aug. 8, 2013

(65) Prior Publication Data
US 2014/0370506 A1    Dec. 18, 2014

Related U.S. Application Data

(60) Provisional application No. 61/593,829, filed on Feb. 1, 2012.

(51) Int. Cl.
C12Q 1/68          (2018.01)
C12Q 1/6834        (2018.01)
C12Q 1/6816        (2018.01)

(52) U.S. Cl.
CPC ......... C12Q 1/6834 (2013.01); C12Q 1/6816 (2013.01)

(58) Field of Classification Search
USPC .......... 435/6.1, 6.11, 6.12, 91.1, 91.2, 91.51, 435/183; 436/94, 501; 536/23.1, 24.3,
(Continued)

(56) References Cited

U.S. PATENT DOCUMENTS 5,866,336 A * 2/1999 Nazarenko ........... C12Q 1/6818
                                                    435/6.12
2004/0033518 A1* 2/2004 Wittwer ............... C12Q 1/6827
                                                    435/6.1

(Continued)

FOREIGN PATENT DOCUMENTS

CN    101050475 A    10/2007
WO    01/94625 A2    12/2001

(Continued)

OTHER PUBLICATIONS

Riccelli et al., Hybridization of single-stranded DNA targets to immobilized complementary DNA probes: comparison of hairpin versus linear capture probes. Nucleic Acids Research, 29, 996-1004, 2001.*

(Continued)

Primary Examiner — Frank W Lu
(74) Attorney, Agent, or Firm — Alston & Bird LLP; Jeff Landes

(57) ABSTRACT

The invention provides an improved stem-loop target capture oligomer and methods of use. Such a target capture oligomer has a target-binding segment forming a loop flanked by stem segments forming a stem. The stem segments are of unequal length. Such probes show little or no binding to immobilized probes in the absence of a target nucleic acid but offer good target sensitivity. The probes are particularly useful in multiplex methods of detection in which multiple target capture oligomers are present for (Continued)

Legend
☐ OPTIONAL SPACER
▧ FIRST STEM
▨ SECOND STEM
▦ TARGET BINDING SEGMENT
● MAGNETIC BEAD
▓ IMMOBILIZED PROBE Asymmetric Target Capture Oligomer Linear Target Capture Oligomer detecting of multiple target nucleic acids (for example, detecting multiple polymorphic forms of a target gene).

10 Claims, 3 Drawing Sheets

Specification includes a Sequence Listing.

(58) Field of Classification Search
USPC .............................................. 536/24.33, 25.3
See application file for complete search history.

(56) References Cited

U.S. PATENT DOCUMENTS

| | | | |
|---|---|---|---|
| 2005/0239734 A1* | 10/2005 | Uhlmann | A61K 39/39 514/44 A |
| 2006/0068417 A1* | 3/2006 | Becker | C12Q 1/6834 435/6.11 |
| 2006/0223777 A1 | 10/2006 | Vermeulen et al. | |
| 2009/0246788 A1* | 10/2009 | Albert | C12Q 1/6827 435/6.12 |

FOREIGN PATENT DOCUMENTS

| | | |
|---|---|---|
| WO | 02/24955 A2 | 3/2002 |
| WO | 2004081520 A2 | 9/2004 |

OTHER PUBLICATIONS

APO Patent Examination Report No. 1, Australian Patent Application No. 2013205603, dated Dec. 23, 2014.
CIPO First Office Action, Chinese Application No. 201380013675.3, dated Jul. 3, 2015.
CIPO Search Report, Chinese Application No. 201380013675.3, dated Jun. 25, 2015.
EPO Communication Pursuant to Article 94(3) EPC, European Patent Application No. 13705870.7, dated Feb. 24, 2016.
EPO Communication Pursuant to Article 94(3) EPC, European Patent Application No. 13705870.7, dated Oct. 10, 2016.
EPO Communication Pursuant to Article 94(3) EPC, European Patent Application No. 13705870.7, dated Jul. 19, 2017.
PCT International Preliminary Report on Patentability, International Application No. PCT/US2013/024499, dated Aug. 5, 2014.
PCT International Search Report, International Application No. PCT/US2013/024499, dated Aug. 7, 2013.
PCT Written Opinion, International Application No. PCT/US2013/024499, dated Aug. 7, 2013.
Ginocchio et al., "Life Beyond PCR: Alternative Target Amplification Technologies for the Diagnostics of Infectious Diseases, Part II," vol. 26(17) p. 129-136, Clinical Microbiology Newsletter, US.
Lucarelli et al., "Electrochemical and Piezoelectric DNA Biosensors for Hybridisation Detection," vol. 609(2) p. 139-159, Analytica Chimica Acta, Amsterdam.
Extended European Search Report for European Application No. 19155762.8 dated Mar. 4, 2019.

* cited by examiner

Asymmetric Target Capture Oligomer

Linear Target Capture Oligomer

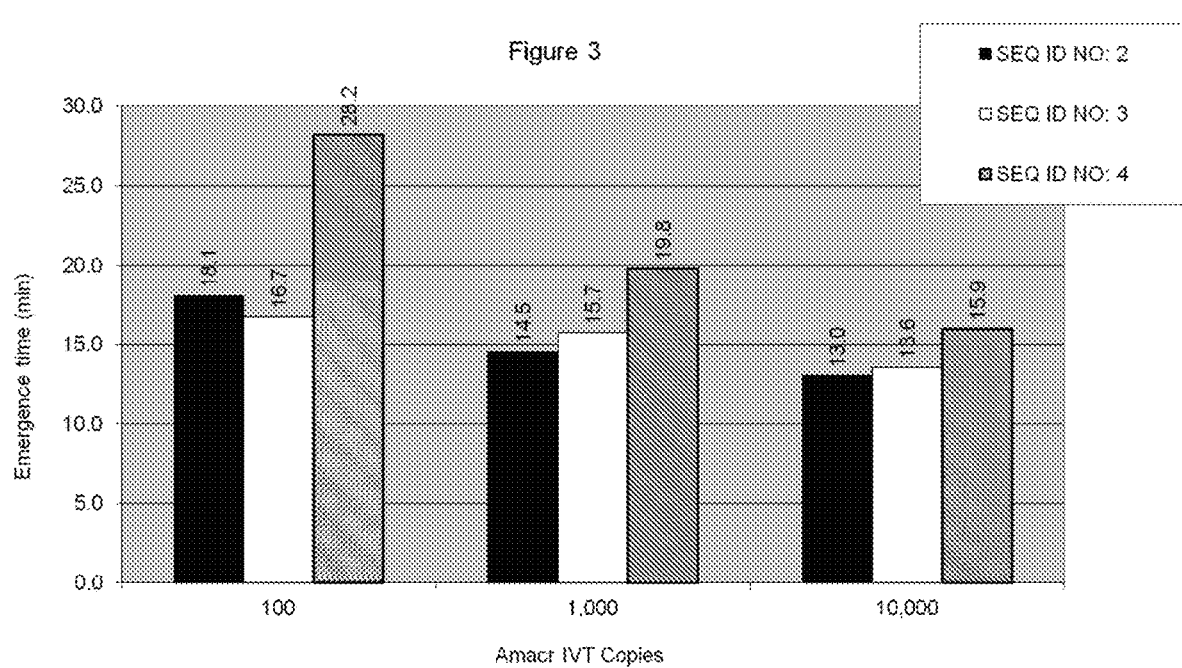
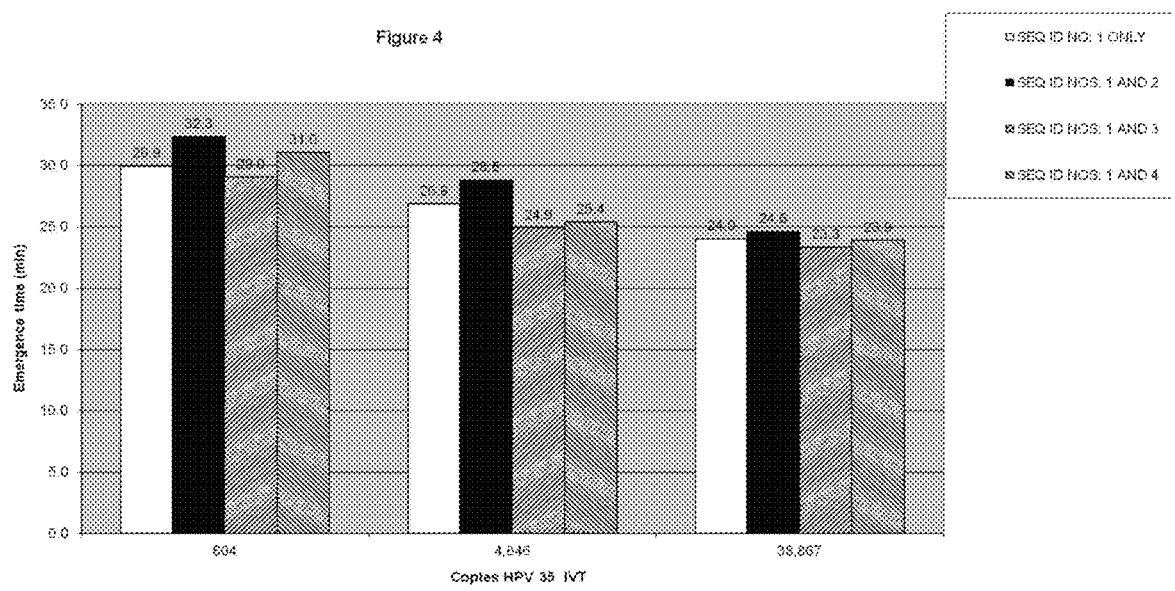

ASYMMETRIC HAIRPIN TARGET CAPTURE OLIGOMERS

CROSS-REFERENCE TO RELATED APPLICATIONS

The present applications is a US national stage of PCT/US2013/024499 filed Feb. 1, 2013, which claims the benefit of claims the benefit of US application no. 61/593,829 filed Feb. 1, 2012 incorporated by reference in its entirety for all purposes.

REFERENCE TO A "SEQUENCE LISTING"

The sequence listing in file 449300 SEQLST.TXT was created Jul. 31, 2014 and is 7,196 bytes, which is hereby incorporated by reference in its entirety for all purposes.

BACKGROUND

Detection of nucleic acids in a sample is useful in diagnostic, therapeutic, forensic, agricultural, food science applications and other areas. One technique for purifying a target polynucleotide, which is often used in diagnostic procedures, involves capturing a target nucleic acid onto a solid support. The solid support retains the target nucleic acid during one or more washing steps of the target nucleic acid purification procedure. The captured target nucleic acid sequence can be analyzed by various methods. One such method uses nucleic acid probes that hybridize to a target sequence. Probes can be designed to detect different target sequences such as those characteristic of microorganisms, viruses, human genes, plant or animal genes, and/or pathogenic conditions. Additional analysis techniques that benefit from captured target nucleic acids include amplification assays, microarrays, sequencing assays, mass spectrometry of nucleic acids.

A target nucleic acid can be captured using a target capture oligomer that hybridizes to bind both to a target nucleic acid and to a nucleic acid fixed to a solid support. The target capture oligomer joins the target nucleic acid to the solid support to produce a complex comprising a bound target nucleic acid. A labeled probe can be hybridized to the bound target and unbound labeled probe can be washed away from the solid support (see Stabinsky, U.S. Pat. No. 4,751,177).

A variation of a target capture oligomer has been described in which in the absence of target the capture probe exists as a stem-loop structure and in the presence of a target nucleic acid, the target nucleic acid binds to the loop portion, opening up the stem and making one of the arms of the loop accessible to bind an immobilized probe (see US 20060068417). Such an arrangement can be useful in reducing the ability of a target capture oligomer to hybridize with an immobilized probe before the target capture oligomer has bound to its target nucleic acid.

SUMMARY OF THE CLAIMED INVENTION

The invention provides target capture oligomers (TACOs) comprising first and second stem segments differing in length by at least two nucleobases flanking a target-binding segment complementary to a target nucleic acid. Under hybridizing conditions in the absence of the target nucleic acid the target capture oligomer forms a stem-loop, intramolecular hybridization of the first and second stem segments forming the stem, and the target-binding segment forming the loop; and in the presence of the target nucleic acid, the target-binding segment hybridizes to the target nucleic acid disrupting the intramolecular hybridization of the first and second stem segments resulting in the first stem segment being accessible to hybridize to a complementary immobilized probe. In some TACOs, the first stem segment comprises at least 15 nucleobase units and the second stem segment comprises at least five nucleobase units. In some TACOs, the length of the second stem segment is 39-61% of the length of the first stem segment. In some TACOs, the first stem segment and the second stem segment differ in length by at least 5 nucleobase units. In some TACOs, the first and second stem segments differ in length by at least 9 nucleobase units. In some TACOs, the first and second stem segments differ in length by 5-15 nucleobase units. In some TACOs, the first segment has 17-26 nucleobase units and the second segment has 7-16 nucleobase units. In some TACOs, the first segment has 18-24 nucleobase units and the second segment has 7-15 nucleobase units and the first segment is at least 7 nucleobase units longer than the second segment. In some TACOs, the first and second stem segments occupy the 5' and 3' ends of the target capture oligomer respectively and the first stem segment is complementary to the immobilized probe. In some TACOs, the first and second stem segment comprises comprise complementary segments of polyA and polyT nucleobase units. In some TACOs, the first segment comprises a polyA segment and the second stem segment comprises a polyT segment. In some TACOs, the first or second stem segment comprises $T_{(0-5)}A_{(10-40)}$. In some TACOs, the first stem segment comprises $T_{(0-5)}A_{(10-40)}$ and the second stem segment comprises $A_{(0-5)}T_{(10-40)}$, wherein the first stem segment is longer than the second stem segment. In some TACOs, the $A_{(10-40)}$ of the first stem segment is 5-15 nucleotides longer than the $T_{(10-40)}$ of the second stem segment. In some TACOs, the first stem segment comprises $A_{(15-40)}$ and the second stem segment comprises $T_{(10-30)}$. In some TACOs, the target binding segment comprises at least one methyoxynucleobase.

The invention further provides a kit comprising a target capture oligomer as defined above and an immobilized probe immobilized probe comprising a support bearing a probe comprising a segment complementary to the first or second hairpin stem segment. In some kits, the longer of the first and second hairpin segments comprises polyA, the shorter of the first and second hairpin segments comprises polyT and the immobilized probe segment comprises polyT, the polyT being intermediate in length between the polyA and polyT segments of the first and second hairpin probes.

The invention further provides methods of capturing a target nucleic acid. Such methods comprise contacting a sample suspected of containing the target nucleic acid with a target capture oligomer and an immobilized probe; the target capture oligomer comprising first and second hairpin stem segments differing in length by at least two nucleobase units flanking a target-binding segment complementary to target nucleic acid, the target capture oligomer being in the form of a hairpin stem-loop, the stem being formed by intramolecular hybridization of the first and second hairpin stem segments and the target-binding segment constituting the loop; the immobilized probe comprising a support bearing a probe comprising a segment complementary to the first or second hairpin stem segment; wherein if the sample contains the target nucleic acid, the target nucleic acid hybridizes to the target-binding segment disrupting the intramolecular hybridization of the first and second hairpin stem segments, as a result of which the first or second hairpin segment hybridizes to the complementary segment on the immobilized probe forming a support-bound capture hybrid; and if the sample does not contain the target nucleic acid the first and second segments remain intramolecularly hybridized as a stem. Any of the target capture oligomers disclosed above or elsewhere in this application can be used in such methods.

In some methods, the target is present in the sample. Some methods further comprise separating the support-bound capture hybrid from the sample. In some methods, the contacting is performed at a first temperature followed by a second temperature lower than the first temperature. In some methods, the first temperature is between the melting point of duplex formed between the first and second stem segments and a duplex formed between the target binding segment and the target nucleic acid and the second temperature is below the melting temperature of the duplex formed form the first and second stem segments and a duplex formed between the second stem segment and the immobilized probe. In some methods, the separating is performed at the second temperature. Some methods further comprise releasing the target nucleic acid from the capture hybrid. Some methods further comprise detecting the target nucleic acid. Some methods further comprise sequencing the target nucleic acid. In some methods the target capture oligomer is one of a plurality of target capture oligomers having different target binding segments complementary to different targets. In some methods the plurality of target capture oligomers comprises at least ten target capture oligomers.

The invention further provides a reaction mixture comprising a target capture oligomer as defined in any preceding claim, an immobilized probe immobilized probe comprising a support bearing a probe comprising a segment complementary to the first or second hairpin stem segment and a target nucleic acid that hybridizes to the target-binding segment of the target capture oligomer.

BRIEF DESCRIPTION OF THE FIGURES

FIG. 3 illustrates graphically the results obtained in Example 2.

FIG. 4 illustrates graphically the results obtained in Example 1.

DEFINITIONS

Figure 1:
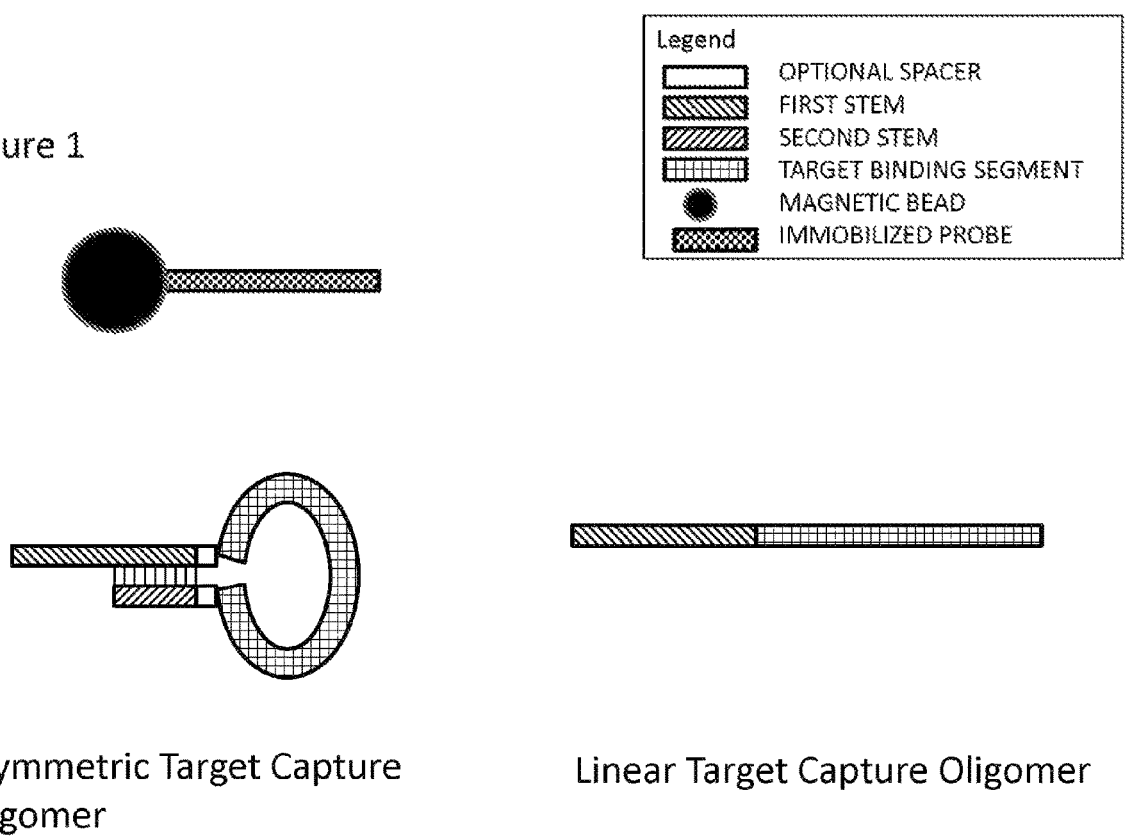
FIG. 1 illustrates the configuration of various target capture oligomers under capture conditions and in the absence of a target nucleic acid to which to hybridize. The black circle with checkered protrusion represents a capture bead and immobilized probe, respectively. An asymmetrical target capture oligomer is shown in the hairpin configuration under such conditions, whereas a linear target capture oligomer remains in a linear configuration. Under these conditions, the first stem of the linear target capture oligomer is available to hybridize with the immobilized probe; however, the first stem of the asymmetric target capture oligomer is not.
Figure 2:
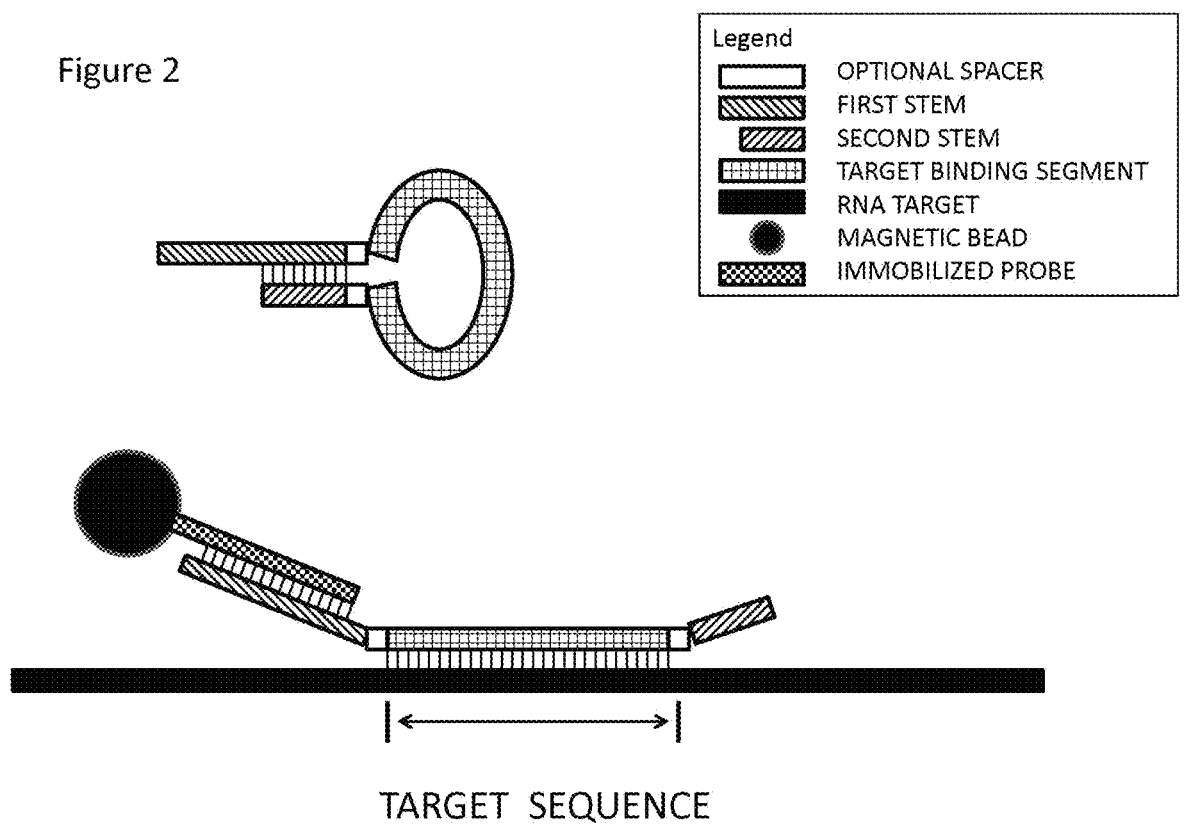
FIG. 2 illustrates the various configurations of an asymmetric target capture oligomers under capture conditions and in the presence of a target nucleic acid to which to hybridize. In this illustration, there is an excess of asymmetric target capture oligomer compared to target nucleic acid. The asymmetrical target capture oligomer bound to the target nucleic acid is shown in the open (non-hairpin) configuration, thereby exposing its first stem for binding with the immobilized probe. The asymmetrical target capture oligomer that is shown in the closed (hairpin) configuration has its second tem bound by its first stem, and not to the immobilized probe.

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobase units. Nucleobase units can be conventional DNA or RNA bases (A, G, C, T, U), base analogs, e.g., inosine, 5-nitroindazole and others (The Biochemistry of the Nucleic Acids 5-36, Adams et al., ed., 11th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxyguanosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; WO 93/13121; Gamper et al., 2004, Biochem. 43(31): 10224-36), and hydrophobic nucleobase units that form duplex DNA without hydrogen bonding (Berger et al., 2000, Nucl. Acids Res. 28(15): 2911-4). Many derivatized and modified nucleobase units or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units. Any of the methods and probes described herein can be practiced with nucleotides.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

Nucleic acids and their component nucleotides can exist in D or L form. The D-form is the natural form. An L-nucleic acid is the enantiomeric form of a D-nucleic acid. The source of stereoisomerism in a nucleic acid resides in the sugar moiety of each monomeric unit forming the nucleic acid. Except for the stereoisomerisms at the sugar moiety of each monomeric unit, D and L-nucleic acids and their monomeric units are closely analogous. Thus, for example, the sugar moieties of an L-nucleic acid can be linked to the same nucleobase units (i.e., adenine, guanine, cytosine, thymine and uracil) as occur in natural DNA or RNA, or any of the many known analogs of these nucleobase units. The sugar moiety of L-nucleic acids can be ribose or deoxyribose or similar compounds (e.g., with 2'-methodyx or 2' halide substitutions). The sugar moieties can be linked by sugar phosphodiester linkages as in D-nucleic acids or by any of the analog linkages that have been used with D-nucleic acids, such as phosphorothioate or methylphosphonate linkages or peptide-nucleic acid linkages.

L-nucleotides incorporating at least the conventional nucleobase units (i.e., A, C, G, T and U) are commercially available in the phosphoramidite form suitable for solid phase synthesis (e.g., ChemGenes Corporation (Wilmington, USA)). L-nucleic acids can be synthesized from L-nucleotides using the same solid phase synthesis procedures as are used for D-nucleic acids (e.g., an ABI synthesizer and standard synthesis protocols). L-nucleotides can also be linked to D-nucleotides by a conventional coupling cycle (see Hauser et al., Nucleic Acids Research, 2006, Vol. 34, No. 18 5101-5111 (2006)), thus permitting synthesis of a chimeric nucleic acid having one segment in D-nucleic acid form and the other in L-nucleic form.

L-nucleic acids hybridize to one another according to analogous principles to D-nucleic acids (e.g., by formation of Watson-Crick or Hoogstein bonds) and have similar stability to hybrids of D-nucleic acids. The duplex formed from L-nucleic acids is a left-handed helix whereas that formed from D-nucleic acids is a right handed helix. Although L-nucleic acids can hybridize to each other, as further illustrated by the Examples, L-nucleic acids and particularly polyA or polyT L-nucleic acids have no ability to hybridize to a complementary segment of a poly A or polyT D-nucleic acid.

Unless otherwise apparent from the context, reference to a nucleic acid or nucleotide without specifying whether the form is D- or L-, includes either or both possibilities. However, the context may indicate that only a D nucleic acid or nucleotide is meant. For example, a nucleic acid occurring in nature would be understood to contain only D-nucleotides regardless whether so designated, as would a segment of a probe that forms a stable duplex with such a nucleic acid.

An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U and G) in a defined portion of a larger oligomer. The resulting oligomer is actually a population of oligomers whose finite number of members is determined by the length and number of bases making up the random portion (e.g., 2exp6 oligomers in a population of oligomers that contains a 6-nt random sequence synthesized by using 2 different bases).

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

Specific binding of a target capture oligomer to a target nucleic or target nucleic acids means binding between a single defined sequence in the first segment of a target capture oligomer and an exactly or substantially complementary segment on target nucleic acid(s) to form a stable duplex. Such binding is detectably stronger (higher signal or melting temperature) than binding to other nucleic acids in the sample lacking a segment exactly or substantially complementary to the single defined target capture oligomer sequence. Non-specific binding of a target capture oligomer to target nucleic acids means that the target capture oligomer can bind to a population of target sequences that do not share a segment having exact or substantial complementarity to a single defined target capture oligomer sequence. Such can be achieved by for example using a randomized sequence in the first segment of the capture probe.

Lack of binding between nucleic acids can be manifested by binding indistinguishable from nonspecific binding occurring between a randomly selected pair of nucleic acids lacking substantial complementarity but of the same lengths as the nucleic acids in question.

"Separating" or "isolating" or "purifying" refers to removing one or more components from a complex mixture, such as a sample. Preferably, a separating, isolating or purifying step removes at least 70%, preferably at least 90%, and more preferably about 95% of the target nucleic acids from other sample components. A separating, isolating or purifying step may optionally include additional washing steps to remove non-target sample components. At least X % refers to a range from X % to 100% inclusive of all whole and partial numbers (e.g., 70%, 82.5%, etc.)

"Release" of a capture hybrid refers to separating one or more components of a capture hybrid from each other, such as separating a target nucleic acid from a capture probe, and/or a target capture oligomer from an immobilized probe. Release of the target nucleic acid strand separates the target from other components of a capture hybrid and makes the target available for binding to a detection probe. Other components of the capture hybrid may remain bound, e.g., the target capture oligomer strand to the immobilized probe on a capture support, without affecting target detection.

Reference to a range of value also includes integers within the range and subranges defined by integers in the range.

Transcription mediated amplification (TMA) is an isothermal nucleic-acid-based method that can amplify RNA or DNA targets a billion-fold in less than one hour's time. TMA technology uses two primers and two enzymes: RNA polymerase and reverse transcriptase. One primer contains a promoter sequence for RNA polymerase. In the first step of amplification, this primer hybridizes to the target RNA at a defined site. Reverse transcriptase creates a DNA copy of the target rRNA by extension from the 3' end of the promoter primer. The RNA in the resulting RNA:DNA duplex is degraded by the RNase activity of the reverse transcriptase. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons reenters the TMA process and serves as a template for a new round of replication.

Reverse-transcriptase PCR (RT-PCR) includes three major steps. The first step is reverse transcription (RT), in which RNA is reverse transcribed to cDNA using reverse transcriptase. The RT step can be performed in the same tube with PCR (using a temperature between 40° C. and 50° C., depending on the properties of the reverse transcriptase used. The next step involves the denaturation of the dsDNA at temperature at or about 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. An annealing temperature about 5° C. below the lowest Tm of the pair of primers is usually used (e.g., at or around 60° C.). RT-PCR utilizes a pair of primers, which are respectively complementary to sequence on each of the two strands of the cDNA. The final step of PCR amplification is DNA extension from the primers with a DNA polymerase, preferably a thermostable taq polymerase, usually at or around 72° C., the temperature at which the enzyme works optimally. The length of the incubation at each temperature, the temperature alterations, and the number of cycles are controlled by a programmable thermal cycler.

Real-time polymerase chain reaction, also called quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

DETAILED DESCRIPTION

I. General

The present application provides an improved stem-loop target capture oligomer and methods of use. The stem-loop target capture oligomer described in US20060068417 has the advantage of reducing binding of empty target capture oligomers to an immobilized probe as discussed in the Background. However, such probes may also have a disadvantage of having reduced sensitivity for target detection due to the barrier of opening up the stem-loop structure before the target nucleic acid can bind to the capture probe. The present stem-loop target capture oligomers retain the advantage of having little or no binding to immobilized probes in the absence of a target nucleic acid but offer improve target sensitivity. The improvement arises from having the arms of the target capture oligomer forming the stem being of unequal length. Although an understanding of mechanism is not required for practice of the invention, it is believed that the unequal length of the arms makes the loop portion of the probe more accessible to binding of the target nucleic acid thereby increasing sensitivity. The present hairpin loop probes are particularly useful in multiplex methods of detection in which multiple target capture oligomers are present for detecting of multiple target nucleic acids (for example, detecting multiple polymorphic forms of a target gene).

II. Target Capture Oligomers

The target capture oligomers of the invention can be subdivided into at least three segments, a nucleic acid target binding segment flanked by first and second stem segments. The target-binding segment is configured to bind to a target nucleic acid either specifically or nonspecifically (see U.S. Pat. No. 6,110,678 and WO 2008/016988). The first and second stem segments are configured to bind to each other, and one of the stem segments, arbitrarily designated as the first stem segment, is also configured to bind to an immobilized probe. The first and second stem segments bind to one another by intramolecular hybridization forming a stem-loop structure with the first and second stem segments forming the stem and the target-binding segment the loop. The stem-loop structure is also sometimes referred to as a hairpin loop. In the absence of target the stem-loop structure forms under hybridization conditions below its melting temperature and the target capture oligomer can be referred to as inactive. When the target nucleic acid is present it binds to the target-binding loop segment separating or keeping separate the stem segments, thus activating the target capture oligomer by allowing the first segment to hybridize to a complementary segment of an immobilized probe. Target capture oligomers can be supplied with the stem-loop structure already formed, or with the stems separate or as mixed population of molecules in some of which the stem is formed and in others not. Regardless of the form of target captured oligomers when supplied, the stem-loop structure can be formed in use when a target capture oligomer is placed under hybridization conditions below its melting temperature.

The target capture oligomer can be represented by the following configuration: A-B-C, in which A and C are the first and second stem segments of unequal length configured to form a double-stranded stem and B is the target-binding segment configured to form a single-stranded loop portion. In this representation either A or C can be considered the 5' end of the probe.

In some capture probes, first stem segment comprises at least 15 nucleobase units and the second stem segment comprises at least 5 nucleobase units. In some capture probes, the second stem segment is 39-61% of the length of the first stem segment. In some capture probes, the first and second stem segments differ in length by at least 2, 3, 4, 5, 6, 7, 8, 9, or 10 nucleobase units, for example a difference of 5-15 nucleobase units, and preferably at least 7 nucleobase units. In some capture probes, the first stem segment has 17-26 nucleobase units and the second stem segment has 7-16 nucleobase units. In some capture probes, the first stem segment has 17-25 nucleobase units and the second stem segment 7-15 nucleobase units and the first stem segment is at least 7 nucleobase units longer than the second stem segment. Some particular examples of the nucleobase lengths of the first and second stem segments forming a target capture oligomer include (listed as length of first segment:length of second segment): (a) a range of lengths from 18:7 to 18:11; (b) a range of lengths from 21:9 to 21:12, (c) a length of 20:10, and (d) a range of lengths from 24:10 to 24:15. Ranges provided for nucleobase units are inclusive of all whole numbers making up the range; meaning, for example, that (a) is a first segment that is 18 nucleobase units in length and a second segment that is 7, 8, 9, 10 or 11 nucleobase units in length. In some probes, the first stem segment has 15-40 nucleobase units and the second stem segment 10-30 nucleobase units. Preferably, the first stem segment in such capture probes is at least 2, 3, 4, 5, 6, 7, 8, 9, or 10 nucleobase units longer, and more preferably at least 7 nucleobase units longer than the second stem segment.

In some capture probes, the longer of the first and second stem segments occupies the 5' end of the target capture oligomer and is configured to bind to a complementary segment on the capture probe. In other capture probes, the longer of the first and second stem segments to occupies the 3' end of the probe and/or for the shorter of the first and second stem segments to be configured to bind to a complementary segment of the immobilized probe.

An example of the relative melting temperature of different duplexes present during a target capture reaction is illustrated by discussing the stem duplex and the target binding segment:target nucleic acid duplex. This melting temperature of a duplex formed between the first and second stem segments is preferably lower than the melting temperature of the duplex formed between the target-binding segment and the target nucleic acid. A relatively low melting temperature of the stem segment can be obtained by designing the first and second stem segments to comprise complementary segments of polyA and polyT nucleobase units with the target binding segment and target nucleic acid duplex including at least some G and C nucleotides. In other words, if the first stem segment comprises polyA, the second stem segment comprises polyT or vice versa. Preferably, the first stem segment which is configured to bind to a complementary segment on the immobilized probe comprises polyA and the second stem segment comprises polyT. The polyA segment of the first stem segment can then hybridize to a polyT segment on the immobilized probe. In some probes the first segment comprises A15-40 (i.e., a homopolymer of 15 to 40 A's) and the second segment comprises T10-30 (i.e., a homopolymer of 10-30 T's). In some such probes, the first stem segment is at least 2, 3, 4, 5, 6, 7, 8, 9, or 10 nucleobase units longer, preferably at least 7 nucleobase units longer, than the second stem segment. Reverse configurations in which T is used in place of A and vice versa are also possible.

The first stem segment as well being configured to bind the second stem segment is configured to bind to an immobilized probe. The first stem segment includes a nucleic acid that is substantially and preferably exactly complementary to a nucleic acid present in the immobilized probes. For example, if the first segment includes a polyA homopolymer, then the nucleic acid of the immobilized probe includes a polyT homopolymer. The melting temperature of the duplex formed between the first stem segment and the immobilized probe is preferably less than that between the first stem segment and the second stem segment. Other things being equal, the melting temperature of the duplex formed between the first and second stem segments is usually higher than that of the duplex formed between the second stem segment and immobilized probe because the former duplex results from intramolecular hybridization and the latter intermolecular hybridization. Differential melting temperatures can be additionally or alternatively be achieved by, for example, having a shorter polyT homopolymer in the immobilized probe than in the second stem segment.

Optionally, the first and second stem segments of the immobilized probe and the complementary segment to the first stem segment in the immobilized probe can be L-nucleic acids, as described in a co-pending application PCT/US2011/052050. Because L-nucleic acids hybridize only to other L-nucleic acids, the use of L-nucleic acids can further increase the specificity of capture of a desired target nucleic acid. For such capture probes, the immobilized probe also has an L-nucleic acid segment complementary to the first segment of the capture probe.

The target-binding segment of the target capture oligomer is typically designed to bind to a target nucleic acid sequence of interest. Optionally, the target-binding segment has 2'-O-methyl linkages or other modified structure to enhance binding. In some capture probes, the target-binding segment is designed to bind to a segment within a particular target nucleic acid and not to (or at least with substantially reduced affinity) other nucleic acids lacking this segment that are present in the sample. In other capture probes, the target-binding segment is designed to bind to a class of target nucleic acids (e.g., any DNA molecule) and does not necessarily substantially discriminate between individual target nucleic acids within the class (e.g., by use of a randomized sequence). Excess target capture oligomer is configured so that the target binding segment does not bind non-target species thereby activating the target capture oligomer. As a result, excess target capture oligomer in the inactive configuration does not duplex with the immobilized probe causing capture of contaminant nucleic acids and/or cause reduced capture efficiency.

For the target-binding segment to bind to a particular target nucleic acid sequence of interest, the target-binding segment can be designed to include a nucleic acid that is substantially and preferably exactly complementary to a corresponding segment of the target nucleic acid. The nucleic acid of such a first segment preferably includes at least 6, 10, 15 or 20 nucleobase units (e.g., nucleotides). For example, the nucleic acid can contain 10-50, 10-40, 10-30 or 15-25 nucleobase units (e.g., nucleotides) complementary to corresponding nucleotides in the target nucleic acid. Here, as elsewhere in the application, ranges for contiguous nucleic acid sequences are fully inclusive of all whole numbers defining or within the range.

For a target capture oligomer to capture a population of related target molecules (e.g., a viral RNA population in a patient sample in which molecules differ from one another by the presence of mutations), the target-binding segment is preferably designed to be complementary to a target segment that is relatively conserved among different members of the population.

For the target binding segment to bind nonspecifically to nucleic acids without necessarily substantially discriminating between different sequences within a class, the target binding segment can include a random polymer sequence made up of all four standard DNA bases (guanine (G), cytosine (C), adenine (A) and thymine (T)) or all four standard RNA bases (G, C, A, and uracil (U)) (see US 2008/0286775) The random sequence can also include one or more base analogs (e.g., inosine, 5-nitroindole) or abasic positions in the random polymer sequence. Such a random polymer sequence can contain one or more sequences of poly-(k) bases, i.e., a random mixture of G and U or T bases (e.g., see Table 1 of WIPO Handbook on Industrial Property Information and Documentation, Standard ST.25 (1998)). Sequences that include G and U/T bases can be chosen for their "wobble" property, i.e., U/T binds G or A, whereas G binds C or U/T. A target capture oligomer having a first segment synthesized with a random polymer sequence is in fact a finite population of oligonucleotides that contain different random polymer sequences made up of the bases included during the synthesis of the random portion. For example, a population of nonspecific target capture oligomers that include a 15 nt random polymer sequence made up of G, C, A and T consists of $4^{15}$ members. The first segment can be designed to bind to DNA sequences preferentially relative to RNA or vice versa (see US 2008-0286775).

As mentioned, the melting temperature of the duplex formed the target-binding segment and the target nucleic acid is preferably higher than the duplex formed between the first and second stem segments, which is in turn preferably higher than between the immobilized probe and its complementary stem segment. The methods can alternatively be performed with approximately equal melting temperatures (i.e., within a range of 3° C.) or with different relative melting temperatures for any or all of these three duplexes The melting temperatures of duplexes can be calculated by conventional equations relating base composition and length of a duplex to its melting temperature as discussed above. Calculation of melting temperature of a stem can also take into account intramolecular hybridization as discussed by e.g., Markham et al., Nucleic Acids Research, 2005, Vol. 33, Web Server issue W577-W58; see also world wide web mfold.rit.albany.edumfold.rna.albany.edu/?q=mfold/dna-folding-form. Selection of polyA or polyT homopolymers for the stem segments of the target capture oligomer and the immobilized probe tends to confer a lower melting temperature than that for a duplex formed between target-binding segment and the nucleic acid target because the latter duplex usually also contains some C-G pairings, which confer greater stability on a duplex than A-T pairings. A higher melting temperature between the target-binding segment and the target nucleic acid allows the hybridization to be performed under conditions of higher stringency in which the target capture oligomer first hybridizes to the target nucleic acid and lower stringency in which the target capture oligomer now hybridized to the target nucleic acid hybridizes to the immobilized probe. When performed in this order, both target capture oligomer and target nucleic acid are in solution when they hybridize in which conditions, hybridization takes place with much faster kinetics.

The target capture oligomer may or may not include additional segments as well as first and second stem segments and target-binding segment. For example, the nucleobase units of the stem segments and target binding segments can be directly connected by a phosphodiester bond (or any of the analogs thereof discussed above) or can be separated by a short spacer or linker region, which may include nucleotides (D- or L), or other molecules, such as PEG typically found in linkers. Examples of non-nucleotide linkers include polysaccharides, peptides, and polypeptides. (See e.g., WO 89/02439, and U.S. Pat. No. 5,585,481). Many different non-nucleotide linkers can be used; one example being a C(9) linker. For example, a target capture oligomer can be configured A-[C(9) linker]-B-C, A-B-[C(9) linker]-C, or A-[C(9) linker]-B-[C(9) linker]-C. If a stem segment is a polyA homopolymer, the stem segment and the target-binding segment can be connected by one or more thymine residues. Likewise if a stem segment is a polyT homopolymer, the stem segment and the target-binding segment can be connected by one or more adenine residues. Thus some target capture oligomers comprise T(0-5) A(10-40) target binding segment and/or A(0-5)T(10-39) with the first segment being longer than the second segment. The nomenclature A(10-40) means 10-40 adenine residues, likewise T(0-5) and 0-5 thymidine residues, and so forth. If the shorter homopolymer segments in such an arrangement (e.g., A(0-5) and T(0-5) are complementary and can thus hybridize to one another, they can also be considered to be components of the first and second stem segments and taken into account in determining a melting temperature of a duplex formed from the first and second stem segments.

Multiple different target capture oligomers can be used in combination in the same reaction. In this case, the different target capture oligomers typically have target-binding segment complementary to different target nucleic acids or different segments within the same target nucleic acid, and the same stem segments, so they can bind immobilized probes having the complementary sequences to one of the stem segments. Use of multiple different target capture oligomers can be useful in capturing a population of related target sequences that may be present in a sample, for example, sequence and/or length variants. For example, in capturing a viral RNA population in which members differ from one another by presence of mutations, multiple target capture oligomers binding to different conserved regions within the viral genome can be used. The number of different target capture oligomers can be at least 1, 2, 5, 10, 20, 50 or 100, for example, 1-100 or 2-50 or 3-25, inclusive of all whole numbers defining or within the range.

The number of target capture oligomers needed to capture a target is typically within a range of 2 nM to 20 nM (see, e.g., U.S. Pat. No. 6,534,273 and e.g., Examples Section of U.S. Pat. No. 6,534,273). In some analyses, the number of target capture oligomers in the reaction exceeds the number of available immobilized probes on magnetic beads. Excess target capture oligomers compared to immobilized probe occur for many reasons. Most commonly, the excess of target capture oligomers arises occurs when a large number of different target capture oligomers are added to a reaction to bind a variety of target nucleic acids that may or may not be present in a sample. Although some target capture oligomers hybridized to their targets may bind to the immobilized probe, other target capture oligomers without target nucleic acids (empty capture probes) may also bind to the immobilized probe. The efficiency of target nucleic acid capture begins to suffer because the immobilized probe becomes saturated with empty capture probes. Thus, some target capture oligomers bound to a nucleic acid target lack an available immobilized probe to which to hybridize and valuable sample is not captured and available for analysis.

Increasing the density of immobilized probe on a support or increasing the number of supports in a target capture reaction is only a limited solution. The surface are of a support is limited so that immobilized probe density is finite. Also too high a concentration of supports in a capture reaction can inhibit downstream reactions, such as amplification of captured target nucleic acid.

The present target capture oligomers that are activated by the presence of a target nucleic acid but otherwise remains inactive in the absence of target nucleic acid provide a solution. Only activated target capture oligomers are configured to hybridize an immobilized probe member. Non-activated target capture oligomers are not in a configuration for hybridizing to an immobilized probe, thereby not saturating the immobilized probe with empty capture probes. The result is that more immobilized probe is available for forming a capture complex, and that less undesired material is present in any post capture reactions or storage environments. Capture efficiency is therefore increased without resorting to a corresponding increase in immobilized probe density on a support and concentration of supports in a reaction.

The concentration of magnetic bead and target capture oligomer used for target capture when the captured target is subsequently subjected to a real-time detection are typically less than an otherwise similar capture reaction subjected to an end-point detection. For example, the concentration of the target capture oligomer in the present methods can be 5-20 pmol per reaction and the reaction volume from about 200 μl to 1 ml. Without being bound by any theory, it is believed higher levels of magnetic bead and target capture oligomer interferes with the sensitivity of real-time detection more so than with the sensitivity of end-point detection.

III. Immobilized Probe

An immobilized probe includes a nucleic acid joined directly or indirectly to a support. As indicated in the description of the capture probe, the nucleic acid is substantially or preferably exactly complementary to a nucleic acid in the capture probe, although may or may not be the same length (number of nucleobase units) as the nucleic acid in the capture probe. The nucleic acid in the immobilized probe preferably contains at least six contiguous nucleobase units and can contain for example 10-45 or 10-40 or 10-30 or 10-25 or 14-25, inclusively, any range being inclusive of all whole numbers defining or within the range. The nucleic acid preferably includes a homopolymer, and more preferably a homopolymer of adenine or thymine. A preferred form of immobilized probe is or includes a homopolymer of 14 thymine residues for use in combination with a target capture oligomer including a first stem segment with a homopolymer of adenine residues. Some immobilized probes include a homopolymeric segment with a few mismatches (e.g., at least 95% of nucleobase residues in a segment of 10-45 residues are T residues). The presence of one or a small number of mismatches can serve to decrease the melting temperature between the immobilized probe and first stem segment below that of the target-binding segment and target nucleic acid (if it not already lower without mismatches).

The nucleic acid moiety of an immobilized probe is typically provided in single-stranded form, or if not, is denatured to single stranded form before or during use.

Any of a variety of materials may be used as a support for the immobilized probes, e.g., matrices or particles made of nitrocellulose, nylon, glass, polyacrylate, mixed polymers, polystyrene, silane polypropylene, and magnetically attractable materials. Monodisperse magnetic spheres are a preferred support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support. The linker can include one or more nucleobases of either D or L-enantiomeric forms not intended to hybridize to the target capture oligomer but to act as a spacer between the nucleic acid of the immobilized probe and its support. As mentioned above, the concentration of immobilized probe bound magnetic supports and target capture oligomer used for target capture is typically less when target capture is coupled to a real-time detection than is the case for an end-point detection because higher concentrations of supports may inhibit the real-time detection sensitivity. For immobilized probe bound magnetic beads, the concentration is preferably 15-25 pg/ml, or about 20 pg/ml of the target capture reaction mix.

IV. Target Nucleic Acid

A target nucleic acid refers to a nucleic acid molecule or population of related nucleic acid molecules that is or may be present within a sample. A target nucleic acid includes a segment (target segment) that hybridizes with the target-binding segment on the target capture oligomer to form a stable duplex. The target segment can be the same or substantially the same length as the nucleic acid of the target-binding segment of the target capture oligomer and exactly or substantially complementarity to this nucleic acid. The target segment can be only a small fraction of the total length of a target nucleic acid. For example, a target nucleic acid can be several thousand nucleotides long and a target segment can be for example, only 10-30 of these nucleotides. A target nucleic acid can exist in different forms, i.e., single-stranded, double-stranded, triple-stranded, or mixtures thereof, such as in a partially double-stranded hairpin structure or partially double-stranded duplex structure, and a target segment can present on any strand (sense or antisense) of the structure. A target nucleic acid can be RNA (e.g., viral RNA, micro RNA, mRNA, cRNA, rRNA, hnRNA or DNA (genomic or cDNA) among others. The target nucleic acid can be from a pathogenic microorganism, such as a virus, bacteria or fungus, or can be endogenous to a patient. A target nucleic acid can be synthetic or naturally occurring. A target nucleic acid can range in length from at least about ten nucleotides to more than 1000 nucleotides or up to 10,000 nucleotides or even greater than 10,000 nucleotides. Target nucleic acids having 25-10,000 nucleotides are common.

Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Ban virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance. Viruses mutate rapidly so that a patient is often infected with a heterogeneous population of viral nucleic acids, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic acid population may be required to provide a high likelihood of identifying all drug resistant mutations or at least all, whose representation as a percentage of the total viral nucleic acid population exceeds a threshold. When the present methods of capturing and amplifying a target nucleic population are coupled to a massively parallel sequencing technique, at least 100,000, or 1,000,000 members of the target nucleic population can be sequenced. Using the present methods, it is possible to identify mutations present at representations of less than, for example, 10%, 1% or 0.1% can be identified. Read lengths of for example at least 100, 500, 1000, 2000, or 5000 nucleotides of target nucleic acid can be obtained.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses.

rRNA is particularly useful for detecting and/or typing pathogenic bacteria. Examples of such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, Lymes disease bacteria, streptococci, or neisseria.

The present methods are particularly useful for detecting small RNAs. For example, small RNAs (about 17-27 nt), such as microRNA (miRNA), small or short interfering RNAs (siRNA), short hairpin RNAs (shRNA), and small nuclear RNAs (snRNA) are difficult to separate from other sample components and/or to detect by using known methods. Small RNAs are often relatively rare in a biological sample which contributes to the difficulty of their detection. Because small RNAs are important regulatory molecules that modulate or silence gene expression via RNA interference (RNAi), they may be important disease preventive or therapeutic agents. Thus, the present method are useful for detecting the presence of small RNA in biological samples to determine their presence, stability, therapeutic efficacy, or other characteristics in a biological sample without necessarily requiring extensive processing or nucleic acid amplification.

V. Sample

A "sample" or "biological sample" refers to any composition or mixture in which a target nucleic acid of interest may be present, including plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a disease or condition, particularly infection by a virus. Other samples of interest include industrial samples, such as for water testing, food testing, contamination control, and the like.

Sample components may include target and non-target nucleic acids, and other materials such as salts, acids, bases, detergents, proteins, carbohydrates, lipids and other organic or inorganic materials. The combination of a sample with a target capture oligomer and immobilized probe can be referred to as a reaction mix.

A sample may or may not be subject of processing to purify or amplify a target nucleic acid before performing the target capture assay described below. It is not, for example, necessary to perform a column binding of elution of nucleic acids. Such a step concentrates and purifies nucleic acids but also can lose a large proportion of the sample. Further processing can include simple dilution of a biological fluid with a lysing solution to more complex (e.g., Su et al., J. Mol. Diagn. 2004, 6:101-107; Sambrook, J. et al., 1989, Molecular Cloning, A Laboratory Manual, 2nd ed., pp. 7.37-7.57; and U.S. Pat. Nos. 5,374,522, 5,386,024, 5,786, 208, 5,837,452, and 6,551,778). Viral RNA samples are often prepared by treating plasma or serum with detergent to release RNA from viruses. Typically, a sample containing a target nucleic acid is heated to inactivate enzymes in the sample and to make the nucleic acids in the sample single-stranded (e.g., 90-100° C. for 2-10 min, then rapidly cooling to 0-5° C.).

VI. Target Capture Assay

A target capture assay is performed using one or more capture probes, an immobilized probe, a sample and a suitable medium to permit hybridization of the target capture oligomer to the target nucleic acid and of target capture oligomer to the immobilized probe. The target sample can be heated (e.g., to 95° C.) before performing the assay to denature any nucleic acids in double-stranded form. The components can be mixed in any order. For example the target capture oligomer can be added to the sample and hybridized with the target nucleic acid in the sample before adding the immobilized probe. However, for an automated assay, it is preferable to minimize the number of adding steps by supplying the target capture oligomer and immobilized probe at the same or substantially the same time. In this case, the order of hybridization can be controlled by performing a first hybridization under conditions in which a duplex can form between the target capture oligomer and the target nucleic acid but which exceeds the melting temperature of the duplex that would form between first and second stem segments of the capture probe and between the target capture oligomer and immobilized probe, and then performing a second hybridization under conditions of reduced stringency, preferably below the melting temperature of the duplexes formed between the first and second stem segments and between the target capture oligomer and the immobilized probe. Stringency can be reduced by lowering the temperature of the assay mix. At the higher temperature, the target binding site duplexes with the target nucleic acid. At the lower temperature, the first and second stem segments of capture probes not bound to the target nucleic acid duplex with one another and the first stem segment of capture probes bound to the target nucleic acid duplexes with the immobilized probe. For example, the higher stringency hybridization can be performed at or around 60° C. and the lower stringency hybridization by allowing cooling to room temperature or 25° C. Stringency can also be reduced by reducing salt concentration or adding or increasing concentration of a chaotropic solvent. In some methods, all steps (with the possible exception of an initial denaturation step at higher temperature to denature double stranded target) can be performed isothermally.

Following formation of the target nucleic acid:capture probe:immobilized probe hybrid (the capture hybrid complex) is separated way from other sample components by physically separating the capture support using any of a variety of known methods, e.g., centrifugation, filtration, or magnetic attraction of a magnetic capture support. The separation is preferably performed at a temperature below the melting temperature of stem-loop structures formed by target capture oligomers so that empty target capture oligomers have no opportunity to denature and thus bind to the capture probe. In some methods, the separation is performed at a temperature less than but within 10° C. of the melting temperature of the stem-loop structure (e.g., at 60° C.) to maintain stringency of hybridization conditions and consequent ability to distinguished matched and unmatched target nucleic acids.

To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., a solution containing Tris and EDTA. See e.g., U.S. Pat. No. 6,110,678) and appropriate conditions (e.g., temperature above the Tm of the components) and then readjusting the conditions to permit reformation of the capture hybrid. However, for ease of handling and minimization of steps, washing preferably rinses the intact capture hybrid attached to the capture support in a solution by using conditions that maintain the capture hybrid. Preferably, capture of the target nucleic acid with washing if performed, removes at least 70%, preferably at least 90%, and more preferably about 95% of the target nucleic acids from other sample components.

The target nucleic acid is then subject to PCR amplification, which in the case of RNA samples is an RT-PCR reaction, preferably without prior release of the target nucleic acid from the capture complex. Although no step is performed with intent to dissociate the target nucleic acid from the target capture oligomer before initiating PCR or RT-PCR, the target nucleic acid may be partially or completely dissociated from the target capture oligomer in the course of thermocycling, particularly in a denaturation step performed at or around 95° C. The PCR reaction can be performed in the same vessel (e.g., a microfuge tube) as the capture step. The PCR reaction involves thermocycling between a high temperature of about 95° C. (e.g., 90-99° C.) for dissociation and a low temperature of about 60° C. e.g., 40-75, or 50-70 or 55-64° C.) for annealing. Typically, the number of complete thermocycles is at least 10, 20, 30 or 40. PCR amplification is performed using one or more primer pairs. A primer pair used for PCR amplification includes two primers complementary to opposite strands of a target nucleic acid flanking the region desired to be sequenced. For sequencing most of a viral genome (e.g., more than 50, 75 or 99%), the primers are preferably located close to the ends of the viral genome. For amplification of related molecules (e.g., mutant forms of the same virus present in a patient sample), the primers are preferably complementary to conserved regions of the target nucleic acid likely to be present in most members of the population. PCR amplification is described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Following PCR amplification, the amplified target can optionally be subject to further processing to purify it and/or modify it to be amenable to a particularly sequencing format. Purification if desired can be performed on a silica column (e.g., a Qiagen gravity flow column). The target nucleic acid binds to the column, where it can be washed and then eluted. The amplified target DNA can also be adapted for some sequencing formats by attachment of an adapter. The amplified DNA can be tailed by Klenow-mediated addition of nucleotides (usually a homopolymer) followed by annealing to an oligonucleotide complementary to the added tail, and ligation. Depending on the sequencing platform used, special adaptors are ligated to the template before sequencing. Such as a SMRT bell adapter is ligated to the sample template for sequencing with a Pacific Biosciences' PacBio RS sequencer (see, e.g., Travers et al. Nucl. Acids Res. (2010) 38 (15): e159).

The amplified target nucleic acid is suitable for sequence analysis by a variety of techniques. The capture of target nucleic acid can be coupled to several different formats of so-called next generation and third generation sequencing methods. Such methods can sequence millions of target templates in parallel. Such methods are particularly useful when the target nucleic acid is a heterogeneous mixture of variants, such as is often the case in a sample from a patient infected with a virus, such as HIV. Among the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a target capture oligomer provides a suitable starting material for emulsion PCR. The beads are mixed with PCR reagents and emulsion oil to create individual micro reactors containing single beads (Margulies et al., Nature 437, 376-80 (2005)). The emulsion is then broken and the individual beads with amplified DNA are sequenced. The sequencing can be pyrosequencing performed for example using a Roche 454 GS FLX sequencer (454 Life Sciences, Branford, Conn. 06405). Alternatively, sequencing can be ligation/detection performed for example using an ABI SOLiD Sequencing System (Life Technologies, Carlsbad, Calif. 92008). In another variation, target nucleic acids are eluted from the target capture oligomer and immobilized in different locations on an array (e.g., the HiScanSQ (Illumina, San Diego, Calif. 92121)). The target nucleic acids are amplified by bridge amplification and sequenced by template directed incorporation of labeled nucleotides, in an array format (Illumina). In another approach, target nucleic acids are eluted from the target capture oligomer and single molecules are analyzed by detecting in real-time the incorporation nucleotides by a polymerase (single molecule real time sequencing or SMRT sequencing). The nucleotides can be labeled nucleotides that release a signal when incorporated (e.g., Pacific Biosciences, Eid et al., Sciences 323 pp. 133-138 (2009) or unlabeled nucleotides, wherein the system measures a chemical change on incorporation (e.g., Ion Torrent Personal Genome Machine (Guilform, Conn. 94080)).

Although captured target nucleic acids can be sequenced by any technique, third generation, next generation or massively parallel methods offer considerable advantages over Sanger and Maxam Gilbert sequencing. Several groups have described an ultra high-throughput DNA sequencing procedure (see. e.g., Cheeseman, U.S. Pat. No. 5,302,509, Metzker et al., Nucleic Acids Res. 22: 4259 (1994)). The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi, Science 281, 363 (1998); Binladin et al., PLoS ONE, issue 2, e197 (February 2007); Rehman et al., American Journal of Human Genetics, 86, 378 (March 2010); Lind et al., Next Generation Sequencing: The solution for high-resolution, unambiguous human leukocyte antigen typing, Hum. Immunol. (2010), doi 10.1016/jhumimm.2010.06.016 (in press); Shafer et al., J Infect Dis. 1; 199(5):610 (2009)). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. More recent work performs DNA sequencing by a synthesis method mostly focused on a photocleavable chemical moiety that is linked to a fluorescent dye to cap the 3'-OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. No. 7,052,839 & U.S. Pat. No. 7,033,762; Kumar et al., U.S. Pat. No. 7,041,812; Sood et al, US Pat. App. No. 2004-0152119; Eid et al., Science 323, 133 (2009)). In sequencing-by-synthesis methodology, DNA sequences are being deduced by measuring pyrophosphate release on testing DNA/polymerase complexes with each deoxyribonucleotide triphosphate (dNTP) separately and sequentially. See Ronaghi et al., Science 281: 363 365 (1998); Hyman, Anal. Biochem. 174, 423 (1988); Harris, U.S. Pat. No. 7,767,400.

Sequencing platforms are further moving away from those that read a plurality of target nucleic acids towards single molecule sequencing systems. Amplification is desirable even for single molecule sequencing schemes because target nucleic acid can be used in preparing the template for sequencing. Earlier systems analyze target nucleic acids in bulk. What this means is that, for example with Sanger sequencing, a plurality of target nucleic acids are amplified in the presence of terminating ddNTPs. Collectively, each termination position read on a gel represents a plurality of amplification products that all terminated at the same nucleobase position. Single molecule sequencing systems use nanostructures wherein the synthesis of a complementary strand of nucleic acid from a single template is performed. These nanostructures are typically configured to perform reads of a plurality of single strand nucleic acids. Each single strand contributes sequence information to the sequence analysis system. See, Hardin et al., U.S. Pat. No. 7,329,492; Odera, US 2003-0190647.

For a further review of some sequencing technologies, see Cheng, Biochem. Biophys. 22: 223 227 (1995); Mardis, Annual Review of Genomics and Human Genetics 9: 387-402 (2008) & Genome Medicine 1 (4): 40 (2009); Eid et al., Science 323, 133 (2009); Craighead et al., U.S. Pat. No. 7,316,796; Lipshutz, et al., Curr. Opinion in Structural Biology., 4:376 (1994); Kapranov et al., Science 296, 916 (2002); Levene et al., U.S. Pat. No. 6,917,726, Korlach et al., U.S. Pat. No. 7,056,661; Levene et al. Science 299, 682 (2003); Flusberg et al., Nature Methods v. 7, no. 6, p. 461 (June 2010); Macevicz, U.S. Pat. No. 6,306,597 & U.S. Pat. No. 7,598,065; Balasubramanian et al., U.S. Pat. No. 7,232,656; Lapidus et al, U.S. Pat. No. 7,169,560; Rosenthal et al., U.S. Pat. No. 6,087,095; Lasken, Curr. Opin. Microbiol. 10(5):510 (2007); Ronaghi et al., Pharmacogenomics. Volume 8, 1437-41 (2007); Keating et al., PLoS One 3(10): e3583 (2008); Pease et al., PNAS USA 91(11):5022 (1994); Lockhart, et al., Nat. Biotechnol. 14(13):1675 (1996); Shendure et al., Science 309, 1728 (2005); Kim et al., Science 316, 1481 (2007); Valouev et al. Genome Research 18 (7): 1051 (2008); Cloonan et al., Nature Methods 5 (7): 613 (2008); Tang et al. Nature Methods 6 (5): 377 (2009); McKernan et al. Genome Research 19 (9): 1527 (2009); Ecker et al., Nature Reviews Microbiology 6, 553 (2008).

VII. Kits

The invention also provides kits for performing the methods for capturing and amplifying targets. Kits contain some and usually all of at least one capture probe, at least one immobilized probe, and at least one primer pair for PCR amplification as described above. In preferred kits, the immobilized probe is immobilized to a magnetized particle, preferably a paramagnetic bead, with homopolymeric oligomers (e.g., polyA, polyT, polyC, or polyG) attached to it that are complementary to a homopolymeric portion of the target capture oligomer in the kit. Kits can also include chemical compounds used in forming the capture hybrid and/or detection hybrid, such as salts, buffers, chelating agents, and other inorganic or organic compounds. Kits can also include reverse transcriptase and a DNA polymerase for performing RT-PCR. Kits can also include chemicals for preparing samples for use in the invention methods which may include individual components or mixtures of lysing agents for disrupting tissue or cellular material and preserving the integrity of nucleic acids. Such compositions include enzymes, detergents, chaotropic agents, chelating agents, salts, buffering agents, and other inorganic or organic compounds. Kits can include any combination of the capture probe, immobilize probe and primer pair components described above which can be packaged in combination with each other, either as a mixture or in individual containers. Kits can also contain instructions for performing the capture methods described above.

Although the invention has been described in detail for purposes of clarity of understanding, certain modifications may be practiced within the scope of the appended claims. All publications including accession numbers, websites and the like, and patent documents cited in this application are hereby incorporated by reference in their entirety for all purposes to the same extent as if each were so individually denoted. To the extent difference version of a sequence, website or other reference may be present at different times, the version associated with the reference at the effective filing date is meant. The effective filing date means the earliest priority date at which the accession number at issue is disclosed. Unless otherwise apparent from the context any element, embodiment, step, feature or aspect of the invention can be performed in combination with any other.

EXAMPLES

Materials and Methods

Methods and reagents for nucleic acid synthesis, hybridization, and detection of labels were used substantially as described below herein, although other routine methods and standard reagents may also be used to achieve equivalent results. Oligonucleotides were synthesized using standard phosphoramidite chemistry (Caruthers et al., 1987, Methods in Enzymol., 154: 287), purified using routine chromatographic methods (e.g., HPLC), and typically stored in a solution of 10 mM Tris, 1 mM EDTA (pH 7.5), at room temperature to −80° C. Transport medium generally comprises 150 mM of hepes free acid, lithium lauryl sulfate at 294 mM or 8%, ammonium sulfate at 100 mM and pH adjusted to 7.5 using lithium hydroxide monohydrate. In the target capture steps illustrated in the examples, magnetic particles were used as the capture support. Target nucleic acids hybridize to the capture support using a target capture oligomer and an immobilized probe. Target capture reagent is generally made from hepes, free acid at 250 mM, Lithium Chloride at 1.88M, EDTA free acid at 100 mM and pH adjusted to 6.4 using Lithium Hydroxide monohydrate. Capture support bound to target nucleic acids were separated from the soluble phase by applying a magnetic field to the outside of the assay container, although those skilled in the art will appreciate that other means of separation may be used. The supernatant containing soluble components was removed, and the hybridization complexes bound to the particles were washed (one to three times with a washing solution of sufficient ionic strength to maintain binding of the captured hybrid to the magnetic particles at the washing temperature, usually about 25° C.). Washing generally is performed at room temperature by suspending the particles in the washing solution, separating particles, and removing the supernatant, and repeating those steps for each wash. Amplification and real-time fluorescent detection were performed on the captured targets as described in the examples.

Detection assays are often designed in which multiple different targets in a sample are to be captured and amplified. In practice, there is often only one or a few of the multiple different targets in a sample, and/or only a small amount of some targets are present in the sample. As a result, excess unhybridized target capture oligomers in the samples can interfere with the capture efficiency of other targets in that sample. One problem leading to interference of capture efficiency is that the concentration of target capture oligomer used to capture each desired species of target nucleic acid in a sample results in high a total concentration of capture oligomer. Target capture oligomers having no captured target nucleic acid can then saturate the solid support, limiting capture of target nucleic acid from the sample. This proposed mechanism or theory about why these unhybridized target capture oligomers interfere with capture efficiency of another species is not limiting on the current invention.

Example 1: Interference with Target Capture Efficiency by Unhybridized Target Capture Oligomers To illustrate that unhybridized target capture oligomers interfere with the efficiency of a target capture reaction, a reaction was set up to capture an HPV target nucleic acid in the presence of linear, symmetrical hairpin and asymmetrical hairpin target capture oligomers designed to capture an alpha-methylacyl-co-A racemase (AMACR) target nucleic acid. The sample includes only an HPV target nucleic acid, not an AMACR target nucleic acid. As a result, the linear, asymmetric hairpin and symmetric hairpin target capture oligomers will be in the target capture reactions as unhybridized target capture oligomers. This example also illustrates that unhybridized asymmetrical hairpin target capture oligomer interferes less with capture efficiency than does unhybridized linear capture probe.

In this example, the target nucleic acid was a HPV 35 E6/E7 in vitro transcript (SEQ ID NO:14). Several target capture reagent mixtures were made, each containing one of the following combinations of target capture oligomers: SEQ ID NOS:1 & 2; 1 & 3 or 1 & 4 or containing SEQ ID NO:1 only, each of which is described in Table 2. Also included in the target capture reagent mixtures was a T7 primer (SEQ ID NO:5). Several sample mixtures were made to contain 604, 4846 or 38867 copies of a target nucleic acid (SEQ ID NO:14) in 200 microliters of a 1:1 mixture of water and sample transport media (Gen-Probe Incorporated, USA, Cat#301032). Target capture reactions were performed by adding 50 microliters of each target capture reagent mixture described immediately above to a separate sample mixture; the various reaction conditions are shown in Table 1. The target capture reaction was performed generally as follows: a 30-min incubation at 60° C., followed by a 30-min incubation at 25° C., followed a first wash using 500 μL of wash buffer at 25° C. and then a second wash using 175 μL of wash buffer at 25° C.

Captured nucleic acids were then amplified and detected in a real-time method of universal transcription mediated amplification reaction (see e.g., US 2011-0003305A1). Captured target nucleic acids were each added to a primerless amplification reagent (Gen-Probe Incorporated, USA, Cat#301032) and incubated for 15 min at 42° C. Following incubation, primers, probe (SEQ ID NOS:6-9) and enzyme reagent (Gen-Probe, Cat#301032) were added to each reaction. A series of separate amplification reactions was then performed on each target capture condition, the reactions proceeded for 80 min at 42° C. Detection was carried out in real-time (see e.g., U.S. Pat. No. 7,713,697 for a discussion of real-time detection using molecular torches). The molecular torch SEQ ID NO:6 included 2′-O-methylribonucleotides, a 9-carbon linker, a Cy5 fluorescent dye and a black hole quencher (Glen Research, USA, Cat#s 205932.01 and 105915-10).

TABLE 1

Reaction Conditions and Results.

| Copies of SEQ ID NO: 14 | 10 pM of SEQ ID NO: 1 | 100 pM of SEQ ID NO: 2 | 100 pM of SEQ ID NO: 3 | 100 pM of SEQ ID NO: 4 | Emergence Time (min) |
|---|---|---|---|---|---|
| 604 | Yes | no | No | no | 29.9 |
| 4846 | Yes | no | No | no | 26.9 |
| 38,867 | Yes | no | No | no | 24.0 |
| 604 | Yes | Yes | No | no | 32.3 |
| 4846 | Yes | Yes | No | no | 28.8 |
| 38,867 | Yes | Yes | No | no | 24.6 |
| 604 | Yes | no | Yes | no | 29.9 |
| 4846 | Yes | no | Yes | no | 24.9 |
| 38,867 | Yes | no | Yes | no | 23.3 |
| 604 | Yes | no | No | yes | 31.0 |
| 4846 | Yes | no | No | yes | 25.4 |
| 38,867 | Yes | no | No | yes | 23.9 |

TABLE 2

Sequences for Example 1.

| SEQ ID NO: | Function | Sequence |
|---|---|---|
| 1 | HPV 35 Standard TCO (linear) | GCUCAUAACAGUAGAGAUCAGUUGUCUCUTTTAAAAAAAAAAAAAAAAAAAAAAAAAAAA |
| 2 | AMACR Standard TCO (linear) | GCAGCACAUCCGACCGCUUGCTTTAAAAAAAAAAAAAAAAAAAAAAAAAAAA |
| 3 | AMACR Asymmetric hairpin TCO | TTTTTTTTTTTTGCAGCACAUCCGACCGCUUGCAAAAAAAAAAAAAAAAAAAAA |
| 4 | AMACR Symmetric hairpin TCO | TTTTTTTTTTTTTTTTTTTTGCAGCACAUCCGACCGCUUGCAAAAAAAAAAAAAAAAAAAAAA |
| 5 | T7 Primer | AATTTAATACGACTCACTATAGGGAGAGTCAGATCTACGCGCCTCACATTTACAACAGGACG |
| 6 | Molecular Torch | GUCCUGUUGUAAAUGUGAGGCGAGGAC |
| 7 | Non-T7 primer | GACAGCTCAGAGGAGGAGGATG |
| 8 | Primer Protection | CATCCTCCTCC |
| 9 | Universal T7 | AATTTAATACGACTCACTATAGGGAGAGTCAGATCTACG |

Emergence times are shown in Table 1 and in FIG. 4. The presence of unhybridized linear target capture oligomer (SEQ ID NO:2) extended the emergence time for amplification and detection of SEQ ID NO:14 (i.e., from 29.9 to 32.3 sec for the 604 copy sample). The increased emergence time is indicative of a lower amount of SEQ ID NO:14 being captured in the reactions having SEQ ID NOS:1 & 2 compared to the reactions having SEQ ID NO:1 alone. The presence of the asymmetric or symmetric hairpin target capture oligomer (SEQ ID NOS:3 and 4 respectively) along with SEQ ID NO:1 interfered less or not at all with emergence times of SEQ ID NO:14 compared with SEQ ID NO:1 alone. These results show that both the asymmetric hairpin target capture oligomer and the symmetric target capture oligomer are useful for reducing interference with target capture efficiency by unhybridized probe compared to linear unhybridized target capture probes.

Example 2: Comparison of Standard Linear TCO to Symmetrical and Asymmetrical Hairpin TCOs to Show Target Capture Efficiency of an IVT The purpose of this example is to compare the sensitivity of an asymmetric hairpin target capture oligomer, a linear target capture oligomer and a symmetrical hairpin target capture oligomer. The target nucleic acid was an AMACR in vitro transcript (SEQ ID NO:15). The target hybridizing sequences of the linear target capture oligomer (SEQ ID NO:2), the symmetrical hairpin target capture oligomer (SEQ ID NO:4 and the asymmetrical hairpin target capture oligomer were configured to hybridize with SEQ ID NO:15. Reaction conditions were as shown in Table 3.

Target capture, amplification and detection reactions were performed generally as described above for example 1, except that the amplification reaction was a real-time reverse transcription mediated amplification reaction (see e.g., U.S. Pat. No. 7,374,885). Amplification and detection oligomers are shown in Table 4.

TABLE 3

Reaction Conditions and Results for Example 2.

| Copies of SEQ ID NO: 15 or Urine Sample ID | 10 pM of SEQ ID NO: 2 | 10 pM of SEQ ID NO: 3 | 10 pM of SEQ ID NO: 4 | Emergence Time (min) |
|---|---|---|---|---|
| 100 | Yes | No | no | 18.1 |
| 1000 | Yes | No | no | 14.5 |
| 10000 | Yes | No | no | 13.0 |
| 100 | no | Yes | no | 16.7 |
| 1000 | no | Yes | no | 15.7 |
| 10000 | no | Yes | no | 13.6 |
| 100 | no | No | yes | 28.2 |
| 1000 | no | No | yes | 19.8 |
| 10000 | no | No | yes | 15.9 |

TABLE 4

Sequences for Example 2.

| SEQ ID NO: | Function | sequence 5' --> 3' |
|---|---|---|
| 10 | Torch | CUGCCAAUUUUUGAGAGAACACGGCAG |
| 11 | T7 Primer | AATTTAATACGACTCACTATAGGGAGACCACAACGGTTTTCTGCCGGTTAGCTGGCCACGATATCAACTATTTGG |

TABLE 4-continued

Sequences for Example 2.

| SEQ ID NO: | Function | sequence 5' --> 3' |
|---|---|---|
| 12 | Non-T7 primer | CCAGGAGATTCAGCGGGGCATACGGATTCTCACC |
| 13 | Blocker | GCAGAAGCUUCCUGACUGGCCAAAUCCACUCAGC |

Average emergence times are provided in Table 3 and FIG. 3. At 100 copies of target nucleic acid (SEQ ID NO:15), the asymmetrical hairpin target capture oligomer (SEQ ID NO:3) had an average emergence time of about 17 minutes, whereas the linear target capture oligomer (SEQ ID NO:2) and the symmetrical hairpin target capture oligomer (SEQ ID NO:4) had average emergence times of about 18 minutes and 28 minutes, respectively. Thus the capture sensitivity for the asymmetrical hairpin target capture oligomer is at least equal to the sensitivity of a linear hairpin capture probe and much better than that of the symmetric capture probe.

TABLE 5

In Vitro Transcripts used in the Examples

| SEQ ID NO: | Sequence 5' -> 3' | Description |
|---|---|---|
| 14 | CCCTATAAAAAAAACAGGGAGTGACCGAAAACGGTCGTACCGAAAACGGTTGC CATAAAAGCAGAAGTGCACAAAAAAGCAGAAGTGGACAGACATTGTAAGGTGC GGTATGTTTCAGGACCCAGCTGAACGACCTTACAAACTGCATGATTTGTGCAA CGAGGTAGAAGAAAGCATCCATGAAATTTGTTTGAATTGTGTATACTGCAAAC AAGAATTACAGCGGAGTGAGGTATATGACTTTGCATGCTATGATTTGTGTATA GTATATAGAGAAGGCCAGCCATATGGAGTATGCATGAAATGTTTAAAATTTTA TTCAAAAATAAGTGAATATAGATGGTATAGATATAGTGTGTATGGAGAAACGT TAGAAAAACAATGCAACAAACAGTTATGTCATTTATTAATTAGGTGTATTACA TGTCAAAAACCGCTGTGTCCAGTTGAAAAGCAAAGACATTTAGAAGAAAAAAA ACGATTCCATAACATCGGTGGACGGTGGACAGGTCGGTGTATGTCCTGTTGGA AACCAACACGTAGAGAAACCGAGGTGTAATCATGCATGGAGAAATAACTACAT TGCAAGACTATGTTTTAGATTTGGAACCCGAGGCAACTGACCTATACTGTTAT GAGCAATTGTGTGACAGCTCAGAGGAGGAGGAAGATACTATTGACGGTCCAGC TGGACAAGCAAAACCAGACACCTCCAATTATAATATTGTAACGTCCTGTTGTA AATGTGAGGCGACACTACGTCTGTGTGTACAGAGCACACACATTGACATACGT AAATTGGAAGATTTATTAATGGGCACATTTGGAATAGTGTGCCCCGGCTGTTC ACAGAGAGCATAA | HPV 35 E6/E7 in vitro transcript |
| 15 | GGGATTGGGAGGGCTTCTTGCAGGCTGCTGGGCTGGGGCTAAGGGCTGCTCAG TTTCCTTCAGCGGGGCACTGGGAAGCGCCATGGCACTGCAGGGCATCTCGGTC GTGGAGCTGTCCGGCCTGGCCCCGGGCCCGTTCTGTGCTATGGTCCTGGCTGA CTTCGGGGCGCGTGTGGTACGCGTGGACCGGCCCGGCTCCCGCTACGACGTGA GCCGCTTGGGCCGGGGCAAGCGCTCGCTAGTGCTGGACCTGAAGCAGCCGCGG GGAGCCGCCGTGCTGCGGCGTCTGTGCAAGCGGTCGGATGTGCTGCTGGAGCC CTTCCGCCGCGGTGTCATGGAGAAACTCCAGCTGGGCCCAGAGATTCTGCAGC GGGAAAATCCAAGGCTTATTTATGCCAGGCTGAGTGGATTTGGCCAGTCAGGA AGCTTCTGCCGGTTAGCTGGCCACGATATCAACTATTTGGCTTTGTCAGGTGT TCTCTCAAAAATTGGCAGAAGTGGTGAGAATCCGTATGCCCCGCTGAATCTCC TGGCTGACTTTGCTGGTGGTGGCCTTATGTGTGCACTGGGCATTATAATGGCT CTTTTTTGACCGCACACGCACTGGCAAGGGTCAGGTCATTGATGCAAATATGGT GGAAGGAACAGCATATTTAAGTTCTTTTCTGTGGAAAACTCAGAAATTGAGTC TGTGGGAAGCACCTCGAGGACAGAACATGTTGGATGGTGGAGCACCTTTCTAT ACGACTTACAGGACAGCAGATGGGGAATTCATGGCTGTTGGAGCAATAGAACC CCAGTTCTACGAGCTGCTGATCAAAGGACTTGGACTAAAGTCTGATGAACTTC CCAATCAGATGAGCATGGATGATTGGCCAGAAATGAAGAAGAAGTTTGCAGAT GTATTTGCAGAGAAGACGAAGGCAGAGTGGTGTCAAATCTTTGACGGCACAGA TGCCTGTGTGACTCCGGTTCTGACTTTTGAGGAGGTTGTTCATCATGATCACA ACAAGGAACGGGGCTCGTTTATCACCAGTGAGGAGCAGGACGTGAGCCCCGC CCTGCACCTCTGCTGTTAAACACCCCAGCCATCCCTTCTTTCAAAAGGGATCC TTTCATAGGAGAACACACTGAGGAGATACTTGAAGAATTTGGATTCAGCCGCG AAGAGATTTATCAGCTTAACTCAGATAAAATCATTGAAAGTAATAAGGTAAAA GCTAGTCTCTAACTTCCAGGCCCACGGCTCAAGTGAATTTGAATACTGCATTT ACAGTGTAGAGTAACACATAACATTGTATGCATGGAAACATGGAGGAACAGTA TTACAGTGTCCTACCACTCTAATCAAGAAAAGAATTACAGACTCTGATTCTAC AGTGATGATTGAATTCTAAAAATGGTTATCATTAGGGCTTTTGATTTATAAAA CTTTGGGTACTTATACTAAATTATGGTAGTTATTCTGCCTTCCAGTTTGCTTG ATATATTTGTTGATATTAAGATTCTTGACTTATATTTTGAATGGGTTCTAGTG AAAAAGGAATGATATATTCTTGAAGACATCGATATACATTTATTTACACTCTT GATTCTACAATGTAGAAAATGAGGAAATGCCACAAATTGTATGGTGATAAAAG TCACGTGAAACAGAGTGATTGGTTGCATCCAGGCCTTTTGTCTTGGTGTTCAT GATCTCCCTCTAAGCACATTCCAAACTTTAGCAACAGTTATCACACTTTGTAA TTTGCAAAGAAAAGTTTCACCTGTATTGAATCAGAATGCCTTCAACTGAAAAA AACATATCCAAAATAATGAGGAAATGTGTTGGCTCACTACGTAGAGTCCAGAG | AMACR IVT |

TABLE 5-continued

In Vitro Transcripts used in the Examples

| SEQ ID NO: | Sequence 5' -> 3' | Description |
|---|---|---|
| | GGACAGTCAGTTTTAGGGTTGCCTGTATCCAGTAACTCGGGGCCTGTTTCCCC<br>GTGGGTCTCTGGGCTGTCAGCTTTCCTTTCTCCATGTGTTTGATTTCTCCTCA<br>GGCTGGTAGCAAGTTCTGGATCTTATACCCAACACACAGCAACATCCAGAAAT<br>AAAGATCTCAGGACCCCCCAGCAAGTCGTTTTGTGTCTCCTTGGACTGAGTTA<br>AGTTACAAGCCTTTCTTATACCTGTCTTTGACAAAGAAGACGGGATTGTCTTT<br>ACATAAAACCAGCCTGCTCCTGGAGCTTCCCTGGACTCAACTTCCTAAAGGCA<br>TGTGAGGAAGGGGTAGATTCCACAATCTAATCCGGGTGCCATCAGAGTAGAGG<br>GAGTAGAGAATGGATGTTGGGTAGGCCATCAATAAGGTCCATTCTGCGCAGTA<br>TCTCAACTGCCGTTCAACAATCGCAAGAGGAAGGTGGAGCAGGTTTCTTCATC<br>TTACAGTTGAGAAAACAGAGACTCAGAAGGGCTTCTTAGTTCATGTTTCCCTT<br>AGCGCCTCAGTGATTTTTCATGGTGGCTTAGGCCAAAAGAAATATCTAACCA<br>TTCAATTTATAAATAATTAGGTCCCCAACGAATTAAATATTATGTCCTACCAA<br>CTTATTAGCTGCTTGAAAAATATAATACACATAAATAAAAAAA | |

What is claimed is:

1. A method of capturing a target nucleic acid, the method comprising:
   contacting a sample suspected of containing the target nucleic acid with a target capture oligomer and an immobilized probe;
   the target capture oligomer comprising first and second hairpin stem segments, which first and second hairpin stem segments are polyA and polyT segments respectively or vice versa differing in length by at least five nucleobase units flanking a target-binding segment complementary to target nucleic acid, the target capture oligomer being in the form of or formable into a hairpin stem-loop, the stem being formed by intramolecular hybridization of the first and second hairpin stem segments and the target-binding segment constituting the loop;
   the immobilized probe comprising an a support bearing a probe comprising a segment complementary to the first or second hairpin stem segment;
   wherein if the sample contains the target nucleic acid, the target nucleic acid hybridizes to the target-binding segment separating or keeping separate the first and second hairpin stem segments, as a result of which the first or second hairpin segment hybridizes to the complementary segment on the immobilized probe forming a support-bound capture hybrid thereby capturing the target nucleic acid; and if the sample does not contain the target nucleic acid, the first and second segments are intramolecularly hybridized as a stem.

2. The method of claim 1, wherein the target nucleic acid is present in the sample.

3. The method of claim 1, further comprising separating the support-bound capture hybrid from the sample.

4. The method of claim 3, wherein the method further comprises following the contacting step, incubating the sample at a first temperature followed by a second temperature lower than the first temperature, wherein the first temperature is between the melting temperature of a duplex formed between the first and second stem segments and the melting temperature of a duplex formed between the target binding segment and the target nucleic acid and the second temperature is below both the melting temperature of the duplex formed between the first and second stem segments and the melting temperature of a duplex formed between the second stem segment and the immobilized probe.

5. The method of claim 4, wherein the separating step is performed at the second temperature.

6. The method of claim 1, further comprising releasing the target nucleic acid from the capture hybrid.

7. The method of claim 1, further comprising detecting the target nucleic acid.

8. The method of claim 7, further comprising sequencing the target nucleic acid.

9. The method of claim 1, wherein the target capture oligomer is one of a plurality of target capture oligomers having different target binding segments complementary to different targets.

10. The method of claim 1, wherein the first hairpin stem segment is a homopolymer of 10-40 adenine residues and the second hairpin stem segment is a homopolymer of 10-30 thymine residues or vice versa.

* * * * *

UNITED STATES PATENT AND TRADEMARK OFFICE
CERTIFICATE OF CORRECTION

PATENT NO. : 10,655,165 B2
APPLICATION NO. : 14/376128
DATED : May 19, 2020
INVENTOR(S) : Carlson et al.

Page 1 of 1

It is certified that error appears in the above-identified patent and that said Letters Patent is hereby corrected as shown below:

In the Claims

Column 35, Claim 1, Line 29:
After "comprising" delete "an"

Signed and Sealed this
Twenty-fifth Day of August, 2020

Andrei Iancu
*Director of the United States Patent and Trademark Office*

SEQUENCE LISTING

<160> NUMBER OF SEQ ID NOS: 15

<210> SEQ ID NO 1
<211> LENGTH: 61
<212> TYPE: DNA
<213> ORGANISM: Artificial Sequence
<220> FEATURE:
<223> OTHER INFORMATION: Synthesized

<400> SEQUENCE: 1
gcucauaaca guagagauca guugucuctt taaaaaaaaa aaaaaaaaaa aaaaaaaaaa    60
a                                                                   61

<210> SEQ ID NO 2
<211> LENGTH: 54
<212> TYPE: DNA
<213> ORGANISM: Artificial Sequence
<220> FEATURE:
<223> OTHER INFORMATION: Synthesized

<400> SEQUENCE: 2
gcagcacauc cgaccgcuug ctttaaaaaa aaaaaaaaaa aaaaaaaaaa aaaa          54

<210> SEQ ID NO 3
<211> LENGTH: 58
<212> TYPE: DNA
<213> ORGANISM: Artificial Sequence
<220> FEATURE:
<223> OTHER INFORMATION: Synthesized

<400> SEQUENCE: 3
tttttttttt tttgcagcac auccgaccgc uugcaaaaaa aaaaaaaaaa aaaaaaaa      58

<210> SEQ ID NO 4
<211> LENGTH: 65
<212> TYPE: DNA
<213> ORGANISM: Artificial Sequence
<220> FEATURE:
<223> OTHER INFORMATION: Synthesized

<400> SEQUENCE: 4
tttttttttt tttttttttt ttgcagcaca uccgaccgcu ugcaaaaaaa aaaaaaaaaa    60
aaaaa                                                               65

```
<210> SEQ ID NO 5
<211> LENGTH: 62
<212> TYPE: DNA
<213> ORGANISM: Artificial Sequence
<220> FEATURE:
<223> OTHER INFORMATION: Synthesized

<400> SEQUENCE: 5
aatttaatac gactcactat agggagagtc agatctacgc gcctcacatt tacaacagga    60
cg                                                                  62

<210> SEQ ID NO 6
<211> LENGTH: 27
<212> TYPE: DNA
<213> ORGANISM: Artificial Sequence
<220> FEATURE:
<223> OTHER INFORMATION: Synthesized

<400> SEQUENCE: 6
guccuguugu aaaugugagg cgaggac                                       27

<210> SEQ ID NO 7
<211> LENGTH: 22
<212> TYPE: DNA
<213> ORGANISM: Artificial Sequence
<220> FEATURE:
<223> OTHER INFORMATION: Synthesized

<400> SEQUENCE: 7
gacagctcag aggaggagga tg                                            22

<210> SEQ ID NO 8
<211> LENGTH: 11
<212> TYPE: DNA
<213> ORGANISM: Artificial Sequence
<220> FEATURE:
<223> OTHER INFORMATION: Synthesized

<400> SEQUENCE: 8
catcctcctc c                                                        11

<210> SEQ ID NO 9
<211> LENGTH: 39
<212> TYPE: DNA
<213> ORGANISM: Artificial Sequence
<220> FEATURE:
<223> OTHER INFORMATION: Synthesized

<400> SEQUENCE: 9
aatttaatac gactcactat agggagagtc agatctacg                          39

<210> SEQ ID NO 10
<211> LENGTH: 27
<212> TYPE: DNA
<213> ORGANISM: Artificial Sequence
<220> FEATURE:
<223> OTHER INFORMATION: Synthesized

<400> SEQUENCE: 10
cugccaauuu uugagagaac acggcag                                       27

<210> SEQ ID NO 11
<211> LENGTH: 75
<212> TYPE: DNA
<213> ORGANISM: Artificial Sequence
<220> FEATURE:
```

<223> OTHER INFORMATION: Synthesized

<400> SEQUENCE: 11

```
aatttaatac gactcactat agggagacca caacggtttt ctgccggtta gctggccacg    60
atatcaacta tttgg                                                     75
```

<210> SEQ ID NO 12
<211> LENGTH: 34
<212> TYPE: DNA
<213> ORGANISM: Artificial Sequence
<220> FEATURE:
<223> OTHER INFORMATION: Synthesized

<400> SEQUENCE: 12

```
ccaggagatt cagcggggca tacggattct cacc                                34
```

<210> SEQ ID NO 13
<211> LENGTH: 34
<212> TYPE: DNA
<213> ORGANISM: Artificial Sequence
<220> FEATURE:
<223> OTHER INFORMATION: Synthesized

<400> SEQUENCE: 13

```
gcagaagcuu ccugacuggc caauccacu cagc                                 34
```

<210> SEQ ID NO 14
<211> LENGTH: 861
<212> TYPE: DNA
<213> ORGANISM: Artificial Sequence
<220> FEATURE:
<223> OTHER INFORMATION: Synthesized

<400> SEQUENCE: 14

```
ccctataaaa aaaacaggga gtgaccgaaa acggtcgtac cgaaaacggt tgccataaaa    60
gcagaagtgc acaaaaaagc agaagtggac agacattgta aggtgcggta tgtttcagga   120
cccagctgaa cgaccttaca aactgcatga tttgtgcaac gaggtagaag aaagcatcca   180
tgaaatttgt ttgaattgtg tatactgcaa acaagaatta cagcggagtg aggtatatga   240 cttttgcatgc tatgatttgt gtatagtata tagagaaggc cagccatatg gagtatgcat   300
gaaatgttta aaattttatt caaaaataag tgaatataga tggtatagat atagtgtgta   360
tggagaaacg ttagaaaaac aatgcaacaa acagttatgt catttattaa ttaggtgtat   420
tacatgtcaa aaaccgctgt gtccagttga aaagcaaaga catttagaag aaaaaaaacg   480
attccataac atcggtggac ggtggacagg tcggtgtatg tcctgttgga aaccaacacg   540
tagagaaacc gaggtgtaat catgcatgga gaaataacta cattgcaaga ctatgtttta   600
gatttggaac ccgaggcaac tgacctatac tgttatgagc aattgtgtga cagctcagag   660
gaggaggaag atactattga cggtccagct ggacaagcaa aaccagacac ctccaattat   720
aatattgtaa cgtcctgttg taaatgtgag gcgacactac gtctgtgtgt acagagcaca   780
cacattgaca tacgtaaatt ggaagattta ttaatgggca catttggaat agtgtgcccc   840
ggctgttcac agagagcata a                                             861
```

<210> SEQ ID NO 15
<211> LENGTH: 2534
<212> TYPE: DNA
<213> ORGANISM: Artificial Sequence
<220> FEATURE:
<223> OTHER INFORMATION: Synthesized

<400> SEQUENCE: 15

```
gggattggga gggcttcttg caggctgctg ggctggggct aagggctgct cagtttcctt      60
cagcggggca ctgggaagcg ccatggcact gcagggcatc tcggtcgtgg agctgtccgg     120
cctggccccg ggcccgttct gtgctatggt cctggctgac ttcggggcgc gtgtggtacg     180
cgtggaccgg cccggctccc gctacgacgt gagccgcttg gccggggca agcgctcgct     240
agtgctggac ctgaagcagc cgcggggagc cgccgtgctg cggcgtctgt gcaagcggtc     300
ggatgtgctg ctggagccct tccgccgcgg tgtcatggag aaactccagc tgggcccaga     360
gattctgcag cgggaaaatc caaggcttat ttatgccagg ctgagtggat ttggccagtc     420
aggaagcttc tgccggttag ctggccacga tatcaactat ttggctttgt caggtgttct     480
ctcaaaaatt ggcagaagtg gtgagaatcc gtatgccccg ctgaatctcc tggctgactt     540
tgctggtggt ggccttatgt gtgcactggg cattataatg gctcttttg accgcacacg      600
cactggcaag ggtcaggtca ttgatgcaaa tatggtggaa ggacagcat atttaagttc     660
ttttctgtgg aaaactcaga aattgagtct gtgggaagca cctcgaggac agaacatgtt     720
ggatggtgga gcacctttct atacgactta caggacagca gatggggaat tcatggctgt     780
tggagcaata gaaccccagt tctacgagct gctgatcaaa ggacttggac taaagtctga     840
tgaacttccc aatcagatga gcatggatga ttggccagaa atgaagaaga gtttgcaga     900
tgtatttgca gagaagacga aggcagagtg tgtcaaatc tttgacggca cagatgcctg     960
tgtgactccg gttctgactt ttgaggaggt tgttcatcat gatcacaaca aggaacgggg    1020
ctcgtttatc accagtgagg agcaggacgt gagcccccgc cctgcacctc tgctgttaaa    1080
cacccccagcc atcccttctt tcaaaaggga tcctttcata ggagaacaca ctgaggagat    1140
acttgaagaa tttggattca gccgcgaaga gatttatcag cttaactcag ataaaatcat    1200
tgaaagtaat aaggtaaaag ctagtctcta acttccaggc ccacggctca agtgaatttg    1260
aatactgcat ttacagtgta gagtaacaca taacattgta tgcatggaaa catggaggaa    1320
cagtattaca gtgtcctacc actctaatca agaaaagaat tacagactct gattctacag    1380
tgatgattga attctaaaaa tggttatcat tagggctttt gatttataaa actttgggta    1440
cttatactaa attatggtag ttattctgcc ttccagtttg cttgatatat ttgttgatat    1500
taagattctt gacttatatt ttgaatgggt tctagtgaaa aaggaatgat atattcttga    1560
agacatcgat atacatttat ttacactctt gattctacaa tgtagaaaat gaggaaatgc    1620
cacaaattgt atggtgataa aagtcacgtg aaacagagtg attggttgca tccaggcctt    1680
ttgtcttggt gttcatgatc tccctctaag cacattccaa actttagcaa cagttatcac    1740
actttgtaat ttgcaaagaa aagtttcacc tgtattgaat cagaatgcct tcaactgaaa    1800
aaaacatatc caaaataatg aggaaatgtg ttggctcact acgtagagtc cagagggaca    1860
gtcagtttta gggttgcctg tatccagtaa ctcggggcct gtttccccgt gggtctctgg    1920
gctgtcagct ttcctttctc catgtgtttg atttctcctc aggctggtag caagttctgg    1980
atcttatacc caacacacag caacatccag aaataaagat ctcaggaccc cccagcaagt    2040
cgttttgtgt ctccttggac tgagttaagt tacaagcctt tcttatacct gtctttgaca    2100
aagaagacgg gattgtcttt acataaaacc agcctgctcc tggagcttcc ctggactcaa    2160
cttcctaaag gcatgtgagg aaggggtaga ttccacaatc taatccgggt gccatcagag    2220
tagagggagt agagaatgga tgttgggtag gccatcaata aggtccattc tgcgcagtat    2280
```

```
ctcaactgcc gttcaacaat cgcaagagga aggtggagca ggtttcttca tcttacagtt    2340
gagaaaacag agactcagaa gggcttctta gttcatgttt cccttagcgc ctcagtgatt    2400
ttttcatggt ggcttaggcc aaaagaaata tctaaccatt caatttataa ataattaggt    2460
ccccaacgaa ttaaatatta tgtcctacca acttattagc tgcttgaaaa atataataca    2520
cataaataaa aaaa                                                      2534
```